United States Patent
Pagan

[11] Patent Number: 6,003,514
[45] Date of Patent: Dec. 21, 1999

[54] LARYNGEAL MASK ASSEMBLIES

[75] Inventor: Eric Pagan, Hythe, United Kingdom

[73] Assignee: Smiths Industries Public Limited Company, London, United Kingdom

[21] Appl. No.: 09/035,203

[22] Filed: Mar. 5, 1998

[30] Foreign Application Priority Data

Mar. 18, 1997 [GB] United Kingdom .................. 9705537

[51] Int. Cl.⁶ ................................................. A61M 16/00
[52] U.S. Cl. ............................... 128/207.15; 128/200.26; 604/96
[58] Field of Search ......................... 128/707.14, 707.15, 128/206.26, 200.26; 604/96, 97, 98, 99, 100, 101, 102, 103

[56] References Cited

U.S. PATENT DOCUMENTS

| Re. 35,531 | 6/1997 | Callaghan et al. | 128/207.15 |
|---|---|---|---|
| 4,995,388 | 2/1991 | Brain | 128/207.15 |
| 5,282,464 | 2/1994 | Brain | 128/207.15 |
| 5,477,851 | 12/1995 | Callaghan et al. | 128/207.15 |
| 5,632,271 | 5/1997 | Brain | 128/207.15 |
| 5,720,275 | 2/1998 | Patil et al. | 128/200.26 |
| 5,743,254 | 4/1998 | Parker | 128/200.26 |
| 5,845,634 | 12/1998 | Parker | 128/200.26 |
| 5,896,858 | 4/1999 | Brain | 128/207.15 |

FOREIGN PATENT DOCUMENTS

| 2205499A | 12/1988 | United Kingdom . |
|---|---|---|
| 97/12641 | 4/1997 | WIPO . |

*Primary Examiner*—John G. Weiss
*Assistant Examiner*—Joseph F. Weiss
*Attorney, Agent, or Firm*—Pollock, Vande, Sande & Amernick

[57] ABSTRACT

A laryngeal mask airway has a tube with a mask portion at its patient end, the tube opening into the center of the mask portion. The mask portion is formed by a mount attached to the tube and by a bag-shape cuff attached to the mount. The mount is formed with two laterally-projecting flaps defining a dumbbell-shape opening to the tube. The flaps deflect the epiglottis during insertion of the airway into the patient but can be deflected by a suction tube, or the like, inserted through the tube.

5 Claims, 1 Drawing Sheet

LARYNGEAL MASK ASSEMBLIES

BACKGROUND OF THE INVENTION

This invention relates to laryngeal mask assemblies

It is common practice to use an airway known as a laryngeal mask for the administration of anaesthetic and ventilation gases to a patient. These airways comprise a tube with an inflatable mask or cuff at one end, the tube being inserted in the patient's mouth so that one end is located in the hypopharynx and so that the mask forms a seal in this region with the surrounding tissue. Laryngeal masks are described in, for example, U.S. Pat. Nos. 5,355,879, 5,305,743, 5,297,547, 5,282,464, GB 2267034, U.S. Pat. Nos. 5,249,571, 5,241,956, 5,303,697, GB 2249959, GB 2111394, EP 448878, U.S. Pat. No. 4,995,388, GB 2205499, GB 2128561 and GB 2298797.

Laryngeal masks have several advantages over endotracheal tubes, which are longer and seal with the trachea below the vocal folds. One problem with laryngeal mask airways, however, is that there is a risk that the epiglottis can enter the air passage through the airway during insertion, thereby causing a blockage. In GB-A-2205499 there is described a laryngeal mask having bars extending across the patient-end opening of the tube into the mask, to prevent the epiglottis from entering the opening.

BRIEF SUMMARY OF THE INVENTION

It is an object of the present invention to provide an improved laryngeal mask assembly.

According to the present invention there is provided a laryngeal mask assembly comprising a tube with a mask portion at its patient end, the tube having an opening into the center of the mask portion, the mask portion having at least one flap member projecting laterally across a part only of the opening, so as to deflect the epiglottis away from the opening during insertion, and the flap member being deflectable by an elongate member inserted along the tube.

The mask portion preferably has two flap members projecting laterally towards one another from opposite sides, both flap members deflecting the epiglottis away from the opening and being deflectable by an elongate member inserted along the tube. The flap members may provide a dumbbell shape to the opening. The mask portion may comprise a mount member attached with the tube and a cuff attached with the mount member, each flap member being formed from the material of the mount member. The cuff may be a bag-shape member attached with the mount member adjacent each flap member.

A laryngeal mask airway assembly according to the present invention, will now be described, by way of example, with reference to the accompanying drawing.

DETAILED DESCRIPTION OF THE PREFERRED EMBODIMENT

Figure 1:
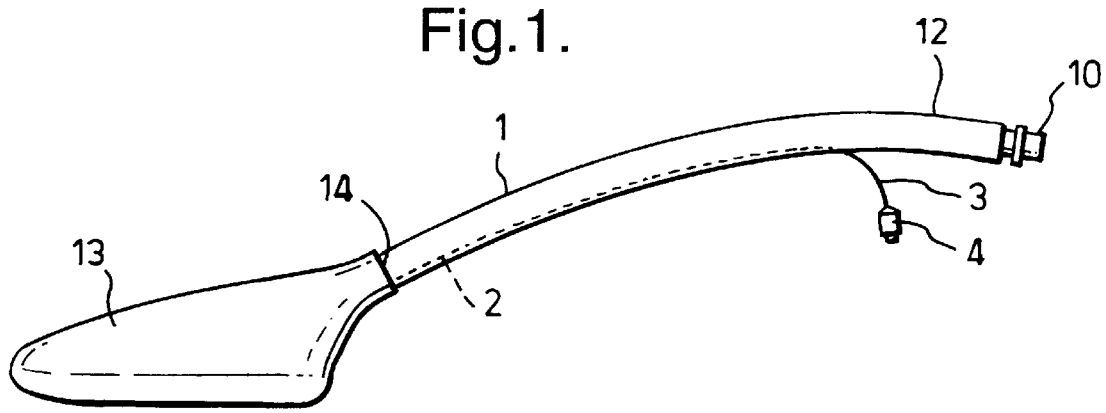
FIG. 1 is a side elevation view of the assembly.
Figure 2:
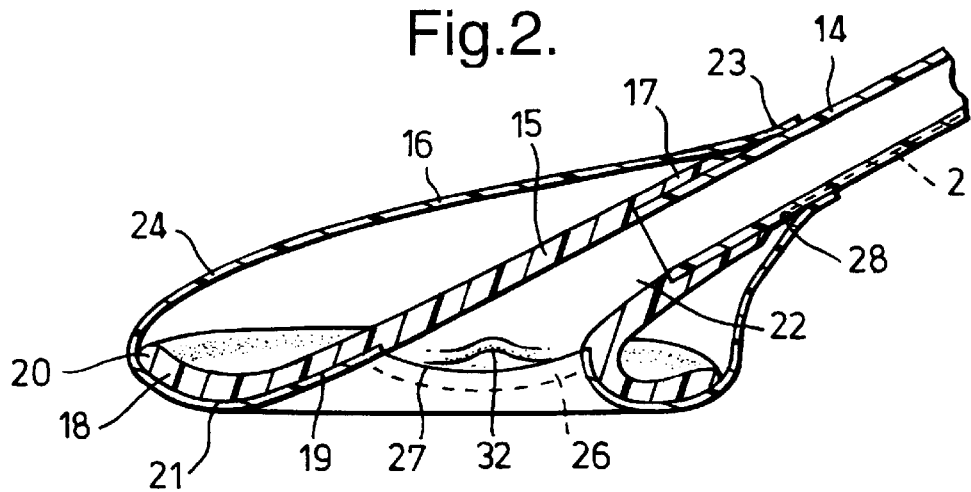
FIG. 2 is a sectional side elevation view of the patient end of the assembly to an enlarged scale.
Figure 3:
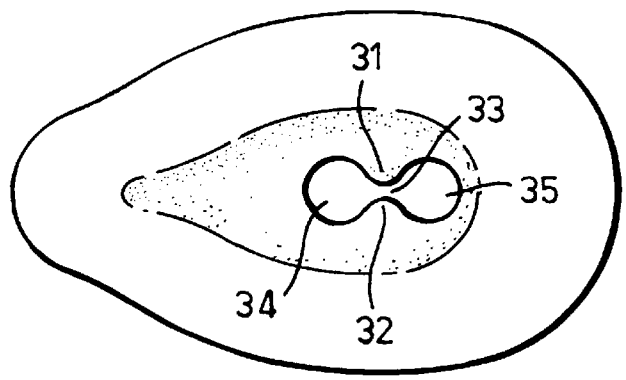
FIG. 3 is a view from below of the patient end of the assembly.

The assembly comprises a bendable tube 1 of a plastics material, such as PVC, with a coupling 10 at its machine end 12. The tube 1 is curved along its length and has a mask portion 13 at its patient end 14.

The tube 1 is extruded with an inflation lumen 2 within its wall. The lumen 2 is connected towards the machine end of the assembly to an inflation line 3 with an inflation indicator and connector 4. The opposite, patient end of the inflation lumen 2 opens into the mask portion 13.

The mask portion 13 comprises a mount member 15 and a flexible bag member 16. The mount member 15 is molded from a bendable plastics material, such as PVC. The mount member 15 has a hollow cylindrical sleeve 17 at its rear end, in which the forward, patient end 14 of the tube 1 is inserted and joined. The forward, patient end 18 of the mount member 15 is of an inverted dish shape with a generally elliptical or egg-shaped outline and with a concave recess 19. The peripheral edge 20 of the mount member 15 is curved rearwardly to form a convex peripheral forward surface 21 lying on a flat plane inclined at an angle of about 30° to the axis of the patient end of the tube 1. The sleeve 17 has a bore 22 at its rear end communicating with the passage through the tube 1, and opens at its forward end into the recess 19.

The bag member 16 is blow molded from a flexible, resilient plastics material, such as PVC, polyurethane, silicone, EVA, TPE, polyether block amide or the like. The bag 16 has a sock shape with an open ankle or neck portion 23 at its upper, rear end and an egg shaped lower, forward foot portion 24 shaped with the same general outline as the mount member 15. The bag 16 encompasses the forward end of the assembly, enclosing the entirety of the mount 15 and having its neck 23 attached to the outside of the forward end 14 of the tube 1, such as by solvent, adhesive or welding. The bag 16 is also attached to the concave recess 19 of the mount 15 along an annular band 26 extending around the opening of the bore 22, to seal the bag material to the mount. A hole 27 in the bag 16 provides an opening to the bore 22 in the mount member 15. The bag 16 provides an inflatable cuff at the forward end of the assembly and communicates with the inflation lumen 2 by means of an opening 28 cut through the outer surface of the tube 1 below the point where the bag is attached to the tube.

The mount member 15 also has an epiglottis deflector provided by two flaps 31 and 32, formed from the material of the mount member, just behind the hole 27 in the bag 16. The flaps 31 and 32 extend parallel to the plane containing the forward surface 21 of the mount member 15 and project laterally inwardly towards the major axis of the elliptical shape of the end of the mount member. The flaps 31 and 32 are of approximately semicircular shape and, at their closest separation, are spaced by a small gap 33. In this way, the opening into the tube 1 is divided into two pear-shaped regions 34 and 35 separated by the gap 33, giving the opening into the bore through the tube a dumbbell or keyhole shape.

The stiffness of the material forming the two flaps 31 and 32 is sufficient to deflect the epiglottis during insertion of the mask assembly, but the flaps bend readily to allow a suction catheter, or the like to be inserted along the tube 1 and project from the mask portion.

What I claim is:

1. A laryngeal mask assembly comprising: a tube having a patient end and a machine end; a mask portion at the patient end of said tube, the tube having an opening into the center of said mask portion; and two flap members projecting laterally towards one another from opposite sides of said opening, so as to deflect the epiglottis away from said opening during insertion of said assembly, said flap members being deflectable by an elongate member inserted along said tube.

2. A laryngeal mask assembly according to claim 1, wherein said flap members provide a dumbbell shape to said opening.

3. A laryngeal mask assembly according to claim 1, wherein said mask portion comprises a mount member attached with said tube and a cuff attached with said mount member, and wherein said flap member is formed from material of said mount member.

4. A laryngeal mask assembly according to claim 3, wherein said cuff is a bag-shape member attached with said mount member adjacent said flap member.

5. A laryngeal mask assembly comprising: a tube having a patient end and a machine end; and a mask portion at the patient end of said tube, wherein the tube has an opening into the center of said mask portion, wherein said mask portion comprises a mount member attached with said tube and a cuff member attached with said mount member, wherein said mount member is formed with two flap members projecting laterally towards on another from opposite ends of said opening, so as to deflect the epiglottis away from said opening during insertion of said assembly, and wherein said flap members are deflectable by an elongate member inserted along said tube.

* * * * *